United States Patent
Zadno-Azizi (12)

(10) Patent No.: US 6,231,588 B1
(45) Date of Patent: May 15, 2001

(54) LOW PROFILE CATHETER FOR ANGIOPLASTY AND OCCLUSION

(75) Inventor: Gholam-Reza Zadno-Azizi, Newark, CA (US)

(73) Assignee: Percusurge, Inc., Sunnyvale, CA (US)

( * ) Notice: Subject to any disclaimer, the term of this patent is extended or adjusted under 35 U.S.C. 154(b) by 0 days.

(21) Appl. No.: 09/128,852

(22) Filed: Aug. 4, 1998

(51) Int. Cl.$^7$ .................................................. A61M 29/00
(52) U.S. Cl. ....................... 606/200; 606/159; 606/194; 604/99.02
(58) Field of Search ............................. 606/1, 110, 113, 606/114, 127, 128, 159, 167, 171, 191–200; 604/93.01, 99.02, 99.011, 101.01, 101.05, 102.01

(56) References Cited

U.S. PATENT DOCUMENTS

| | | |
|---|---|---|
| Re. 34,633 | 6/1994 | Sos et al. . |
| 3,996,938 * | 12/1976 | Clark .................................. 606/198 |
| 4,456,011 | 6/1984 | Warnecke . |
| 4,610,662 | 9/1986 | Weikl et al. . |
| 4,650,466 | 3/1987 | Luther . |
| 4,696,668 | 9/1987 | Wilcox . |
| 4,723,549 | 2/1988 | Wholey et al. . |
| 4,762,129 | 8/1988 | Bonzel . |
| 4,781,677 | 11/1988 | Wilcox . |
| 4,793,350 | 12/1988 | Mar et al. . |
| 4,794,928 | 1/1989 | Kletschka . |
| 4,884,573 | 12/1989 | Wijay et al. . |
| 4,885,003 | 12/1989 | Hillstead . |
| 4,909,252 | 3/1990 | Goldberger . |
| 4,911,163 | 3/1990 | Fina . |
| 4,921,478 | 5/1990 | Solano et al. . |
| 4,921,484 * | 5/1990 | Hillstead ................................ 604/104 |
| 4,946,466 | 8/1990 | Pinchuk et al. . |
| 4,976,720 | 12/1990 | Machold et al. . |
| 5,000,743 | 3/1991 | Patel . |
| 5,049,132 | 9/1991 | Shaffer et al. . |
| 5,053,008 | 10/1991 | Bajaj . |
| 5,059,176 | 10/1991 | Winters . |
| 5,059,178 | 10/1991 | Ya . |
| 5,064,416 | 11/1991 | Newgard et al. . |
| 5,090,958 | 2/1992 | Sahota . |
| 5,152,277 | 10/1992 | Honda et al. . |
| 5,159,937 | 11/1992 | Tremulis . |
| 5,160,321 | 11/1992 | Sahota . |
| 5,163,905 | 11/1992 | Don Michael . |
| 5,163,906 | 11/1992 | Ahmadi . |
| 5,242,396 * | 9/1993 | Evard ........................................ 604/96 |
| 5,304,132 | 4/1994 | Jang . |

(List continued on next page.)

FOREIGN PATENT DOCUMENTS

| | | |
|---|---|---|
| 0 551 184 A1 | 7/1993 | (EP) . |
| 0 747 021 A2 | 12/1996 | (EP) . |
| 0 747 088 A1 | 12/1996 | (EP) . |
| 0 791 340 A1 | 8/1997 | (EP) . |
| 0 820 784 A2 | 1/1998 | (EP) . |
| WO 95/09024 | 4/1995 | (WO) . |
| WO 96/39998 | 12/1996 | (WO) . |
| WO 97/17889 | 5/1997 | (WO) . |
| WO 97/24154 | 7/1997 | (WO) . |
| WO 98/33443 | 8/1998 | (WO) . |
| WO 98/46297 | 10/1998 | (WO) . |

*Primary Examiner*—Glenn K. Dawson
(74) *Attorney, Agent, or Firm*—Knobbe, Martens, Olson & Bear (57) ABSTRACT

A low profile device for simultaneous angioplasty and occlusion includes an angioplasty balloon and an occlusion element which adjoin a common catheter. The occlusion element may be either self-expanding (in which case it is deployed with a sheath that surrounds the catheter) or non-self-expanding (in which case it is deployed with a pull wire that passes through the catheter). The angioplasty balloon is inflated with fluid that either passes through the catheter or a separate tube (or lumen) that adjoins the catheter.

24 Claims, 9 Drawing Sheets

U.S. PATENT DOCUMENTS

| | | | |
|---|---|---|---|
| 5,311,858 | * 5/1994 | Adair | 606/127 |
| 5,312,340 | 5/1994 | Keith . | |
| 5,318,535 | 6/1994 | Miraki . | |
| 5,320,604 | 6/1994 | Walker et al. . | |
| 5,320,605 | 6/1994 | Sahota . | |
| 5,324,263 | 6/1994 | Kraus et al. . | |
| 5,342,306 | 8/1994 | Don Michael . | |
| 5,344,402 | 9/1994 | Crocker . | |
| 5,405,322 | 4/1995 | Lennox et al. . | |
| 5,423,742 | 6/1995 | Theron . | |
| 5,437,637 | * 8/1995 | Lieber et al. | 604/96 |
| 5,454,788 | 10/1995 | Walker et al. . | |
| 5,456,667 | 10/1995 | Ham et al. . | |
| 5,458,574 | 10/1995 | Machold et al. . | |
| 5,460,610 | 10/1995 | Don Michael . | |
| 5,462,529 | 10/1995 | Simpson et al. . | |
| 5,490,859 | 2/1996 | Mische et al. . | |
| 5,501,694 | 3/1996 | Ressemann et al. . | |
| 5,505,699 | 4/1996 | Forman et al. . | |
| 5,522,800 | 6/1996 | Crocker . | |
| 5,540,658 | 7/1996 | Evans et al. . | |
| 5,540,707 | 7/1996 | Ressemann et al. . | |
| 5,558,643 | 9/1996 | Samson et al. . | |
| 5,607,466 | 3/1997 | Imbert et al. . | |
| 5,637,086 | 6/1997 | Ferguson et al. . | |
| 5,683,411 | 11/1997 | Kavteladze et al. . | |
| 5,728,065 | * 3/1998 | Follmer et al. | 604/96 |
| 5,766,203 | 6/1998 | Imran et al. . | |
| 5,769,816 | 6/1998 | Barbut et al. . | |
| 5,769,871 | * 6/1998 | Kelly et al. | 606/200 |
| 5,814,064 | 9/1998 | Daniel et al. . | |
| 5,827,324 | 10/1998 | Cassell et al. . | |
| 5,911,734 | * 6/1999 | Tsugita et al. | 606/200 |
| 5,941,896 | 8/1999 | Kerr . | |

\* cited by examiner

LOW PROFILE CATHETER FOR ANGIOPLASTY AND OCCLUSION

BACKGROUND OF THE INVENTION

1. Field of the Invention

The present invention relates generally to catheters that treat a stenosis site while simultaneously providing occlusion, and more generally to low profile catheters.

2. Description of the Related Art

Coronary heart disease is an extremely common disorder and is the leading cause of death in the U.S. Damage to, or malfunction of, the heart may be caused by narrowing or blockage of the coronary arteries (atherosclerosis) that supply blood to the heart. Myocardial infarction (i.e., dying or dead heart muscle) can result from atherosclerosis, especially from an occlusive or near occlusive thrombus that overlies or is adjacent to atherosclerotic plaque. Thrombi and emboli often result in myocardial infarction, and these clots can block the coronary arteries, or can migrate further downstream, causing additional complications. Should a blockage form at a critical place in the circulatory system, serious and permanent injury, or even death, can occur. To prevent this, some form of medical intervention is usually performed when significant blockage is detected.

Various intervention techniques have been developed to reduce or remove blockage in a blood vessel, allowing increased blood flow through the vessel. One technique for treating stenosis or occlusion of a blood vessel is balloon angioplasty. Generally, a percutaneous or arterial sheath is introduced through a puncture or incision in the patient's skin to provide percutaneous access to blood vessels. This is followed by insertion of a balloon catheter through the arterial sheath and its advancement through the blood vessels to the target site, where the occluded blood vessel is then dilated. The catheters are commonly guided through blood vessels by thin wires called guidewires, which may be either solid or hollow.

Angioplasty balloon catheters can be roughly divided into three categories: over-the-wire (OTW) systems, single-operator-exchange (SOE) or monorail systems, and fixed-wire systems (also called "balloon-on-a-wire"). In an OTW system, a solid guidewire is used to guide a balloon catheter, which is tracked coaxially over the guidewire and can be moved relative to it. SOE balloon catheters are modified OTW catheters, i.e., only the distal portion of a SOE balloon catheter tracks coaxially over the guidewire. In a fixed-wire system, tubing is in fluid communication with a balloon mounted at its distal end to supply inflation fluid to the balloon. The tubing typically has a soft tip at its distal end to guide the placement in the vessel.

It can be difficult, however, to treat plaque deposits and thrombi in the coronary arteries, since the coronary arteries are small, making it difficult to access them with commonly used catheters. Vessels as small as 3 mm in diameter are commonly found in the coronary arteries, and even the diameter of certain saphenous vein bypass graft vessels can be as small as 3 or 4 mm.

The application of balloon angioplasty to certain blood vessels has been limited by the risk of forming emboli during the procedure. For example, when angioplasty is applied to lesions in the carotid artery, there is the possibility of dislodging plaque from the lesion, which can enter the various arterial vessels of the brain and cause permanent brain damage.

Another angioplasty-related complication stems from the wide range of sizes of the emboli resulting from the procedure. Although definitive studies are not available, it is believed that emboli may have diameters anywhere from tens to a few hundred micrometers. More specifically, emboli which are considered dangerous to the patient may have diameters as large as 200 to 300 micrometers or even greater. Thus, an effective emboli containment and/or removal system must be able to accommodate relatively large embolic particles while still fitting within relatively small vessels.

These difficulties are not limited to, say, the carotid arteries. Indeed, balloon dilatation of saphenous vein grafts is more likely to produce symptomatic embolization than dilatation of the coronary arteries, not only because of the difference in the plaque, but also because vein grafts and their atheromatous plaques are generally larger than the coronary arteries to which they are anastomosed. Therefore, balloon angioplasty of vein grafts is performed with the realization that involvement by friable atherosclerosis is likely. Because of these complications and high recurrence rates, angioplasty and atherectomy are generally contraindicated for old, diffusely diseased saphenous vein grafts, thereby limiting the options available for minimally invasive treatment. However, some diffusely diseased or occluded saphenous vein grafts may be associated with acute ischemic syndromes, necessitating some form of intervention.

Yet another difficulty with angioplasty is the limited time available to perform the emboli removal procedure. That is, in order to contain the emboli produced as a result of intravascular therapy, the vessel is generally occluded, meaning that no blood perfuses through the vessel to the end organ. Thus, depending upon the end organ, the complete angioplasty procedure, including time for therapeutic treatment as well as exchanges of angioplastic balloons, stents, and the like, must generally be completed within just a few minutes.

Accordingly, there is a need for a low profile angioplasty device that provides containment of emboli and other particulates.

SUMMARY OF THE INVENTION

The present invention satisfies the need for a low profile device that reduces the risk from emboli by simultaneously providing occlusion, preferably at the distal end of the device.

In one embodiment of the present invention, there is provided a low profile device by incorporating an occlusion device and an angioplasty device onto a common catheter. This substantially reduces the cross section of the device, making the treatment of narrow vessels possible, while guarding against complications that can arise from emboli and other particulates.

In another embodiment, an angioplasty apparatus includes a catheter and a therapy balloon that adjoins the catheter, in which the balloon is inflatable to permit a stenosis site in a vessel to be enlarged. The apparatus further includes a mechanically deployed occlusion element, in which the occlusion element adjoins the catheter and is preferably located distal to the balloon. The occlusion element is expandable to permit the vessel to be at least partially occluded.

In one preferred embodiment, the angioplasty apparatus further comprises a sheath for deploying the occlusion element, in which the sheath surrounds the catheter. The balloon may be in fluid communication with the interior of the catheter, permitting the balloon to be inflated and deflated, or alternatively, the catheter may comprise two lumens, in which one of the lumens is in fluid communication with the balloon.

In another preferred embodiment, the angioplasty apparatus further includes a pull wire for deploying the occlusion element, in which the catheter surrounds the pull wire. The apparatus may further include a hole (an opening, passageway, etc.) in the catheter so that the catheter and the balloon are in fluid communication, and also include a sealing member that adjoins the pull wire, in which the sealing member makes an internal seal as the occlusion element is deployed to isolate the distal end of the catheter from the balloon. The apparatus may further include a second hole in the catheter as well as a hole in the pull wire, so that fluid can be aspirated from outside of the catheter and directed through the second hole in the catheter and then through the hole in the pull wire.

DETAILED DESCRIPTION OF THE PREFERRED EMBODIMENTS

The embodiments disclosed herein comprise a low profile catheter to which both an angioplasty balloon and a mechanically deployed (i.e., not deployed by inflating) occlusion element are attached. If the occlusion element is self-expanding, it is deployed by retracting a sheath, whereas a nonself-expanding occlusion element can be deployed by retracting a pull wire.

1. Low profile catheters with self-expanding occlusion elements

Figure 1A:
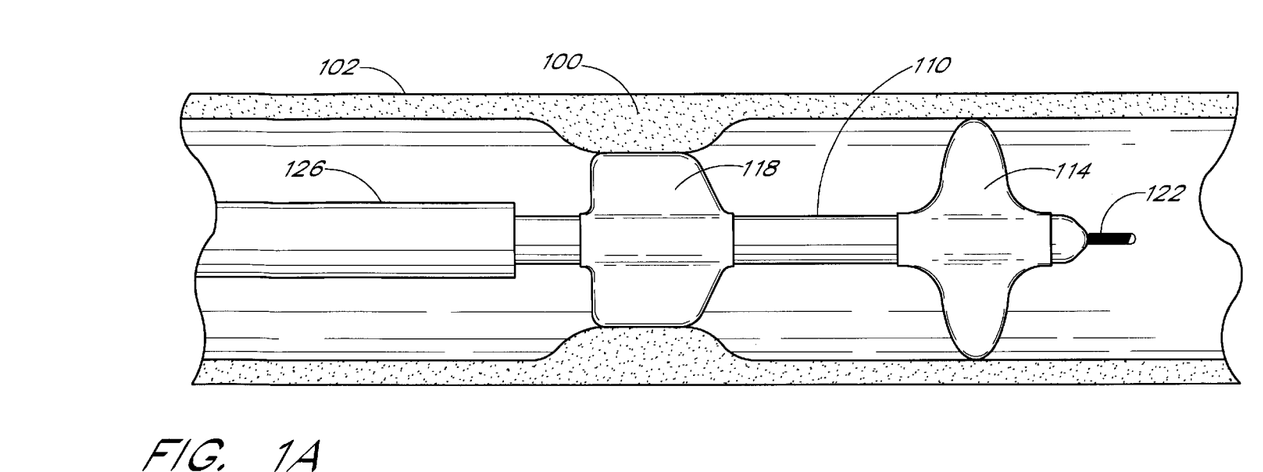
FIG. 1A is a longitudinal view of one embodiment of the invention in which an angioplasty balloon and a distal self-expanding occlusion element both adjoin a therapy catheter, and the occlusion element is deployed with a catheter sheath.

One preferred embodiment of the present invention is shown in FIG. 1A, in which a stenosis site 100 of a vessel 102 is to be treated. A therapy catheter 110 has a self-expanding, mechanically deployed occlusion element 114 near its distal end and an angioplasty balloon 118 which is positioned at the stenosis site 100 during treatment. Alternatively, the occlusion element in the embodiments disclosed herein may be located proximal to the angioplasty balloon. The therapy catheters disclosed herein preferably have an inside diameter (ID.) of 0.017", a wall thickness of 0.003", and may be constructed from polyethylene, polyimid, or Pebax, which may be braided for enhanced flexibility. An integral guidewire tip 122 (e.g., platinum or gold) at the distal end of the therapy catheter 110 aids in positioning the catheter 110 in the vessel 102. Prior to treatment, a catheter sheath 126 surrounds the angioplasty balloon 118 and the occlusion element 114, with the occlusion element being deployed by retracting the catheter sheath. Those expansion members disclosed herein which are deployed with a catheter sheath are self-expanding. When deployed, the occlusion element 114 prevents emboli and other particulates formed during the angioplasty procedure from moving downstream. Following treatment, the catheter sheath 126 is removed from the vessel.

Figure 1B:
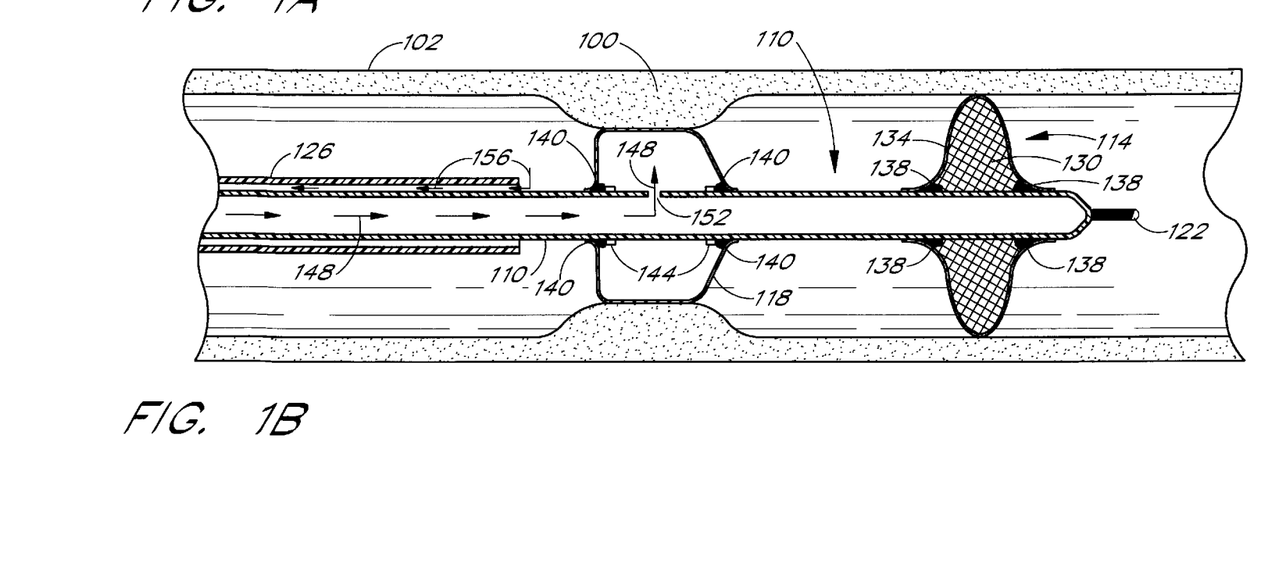
FIG. 1B is a longitudinal cross sectional view of the embodiment of FIG. 1A, illustrating how the angioplasty balloon is inflated with fluid that passes through the therapy catheter.

FIG. 1B shows the corresponding cross sectional view of the embodiment of FIG. 1A. The mechanically deployed occlusion element 114 preferably includes an expansion member 130 surrounded by a membrane 134 that contacts the wall of the vessel 102 when the expansion member expands. The expansion members discussed herein may be made from such materials as stainless steel 304 or 400, Elgiloy, titanium, superelastic or heat activated Nitinol, an iron base shape memory alloy, and a polymer (such as polyethylene or polypropylene). From the structural standpoint, the expansion members may include braids, coils, ribs, ribbon-like structures, slotted tubes, and filter-like meshes, as discussed in Assignee's co-pending U.S. application Ser. No. 09/026,106, filed Feb. 19, 1998 (Atty. Docket No. PERCUS.001CP2), entitled OCCLUSION OF A VESSEL, now abandoned, the entirety of which is hereby incorporated herein by reference. The occlusion element 114 may be secured to the therapy catheter 110 with adhesives, for example. The membrane 134 facilitates the making of a seal with the vessel 102, and may be either impervious to the flow of blood or perforated to allow the passage of blood cells (nominally 6–10 microns in diameter) while still blocking larger particulates such as emboli.

As indicated in FIG. 1B, the angioplasty balloon 118 may be secured to the therapy catheter 110 with adhesives 140. For X-ray positioning of the balloon 118, one or more radiopaque, metallic rings 144 are preferably secured to the therapy catheter 110. In the embodiment of FIGS. 1A and 1B, the balloon 118 is inflated (generally up to 2 to 20 atmospheres) by passing fluid 148 (such as a saline solution or contrast medium such as renographin) into the therapy catheter 110, through one or more holes 152 in the therapy catheter, and into the balloon 118. Following the treatment, the fluid 148 is aspirated from the balloon 118, so that the balloon returns to its placid state. Although aspiration out of the balloon 118 preferably occurs through the catheter 110, separate aspiration lumens may be used in the embodiments disclosed herein, although these may increase the profile of the device. Once the balloon 118 has been deflated, the volume around the balloon is preferably aspirated to remove any emboli or other particulates that form during the angioplasty procedure. This is preferably done by withdrawing blood between the catheter sheath 126 and the therapy catheter 110 in the direction indicated by arrow 156, although a separate lumen (not shown) in the therapy catheter 110 may be used for this purpose. The balloons disclosed herein are preferably made of PET, polyethylene, Nylon, or composite materials, and may have a thickness of between 0.002 and 0.005".

Figures 2A, 2B, 2C:
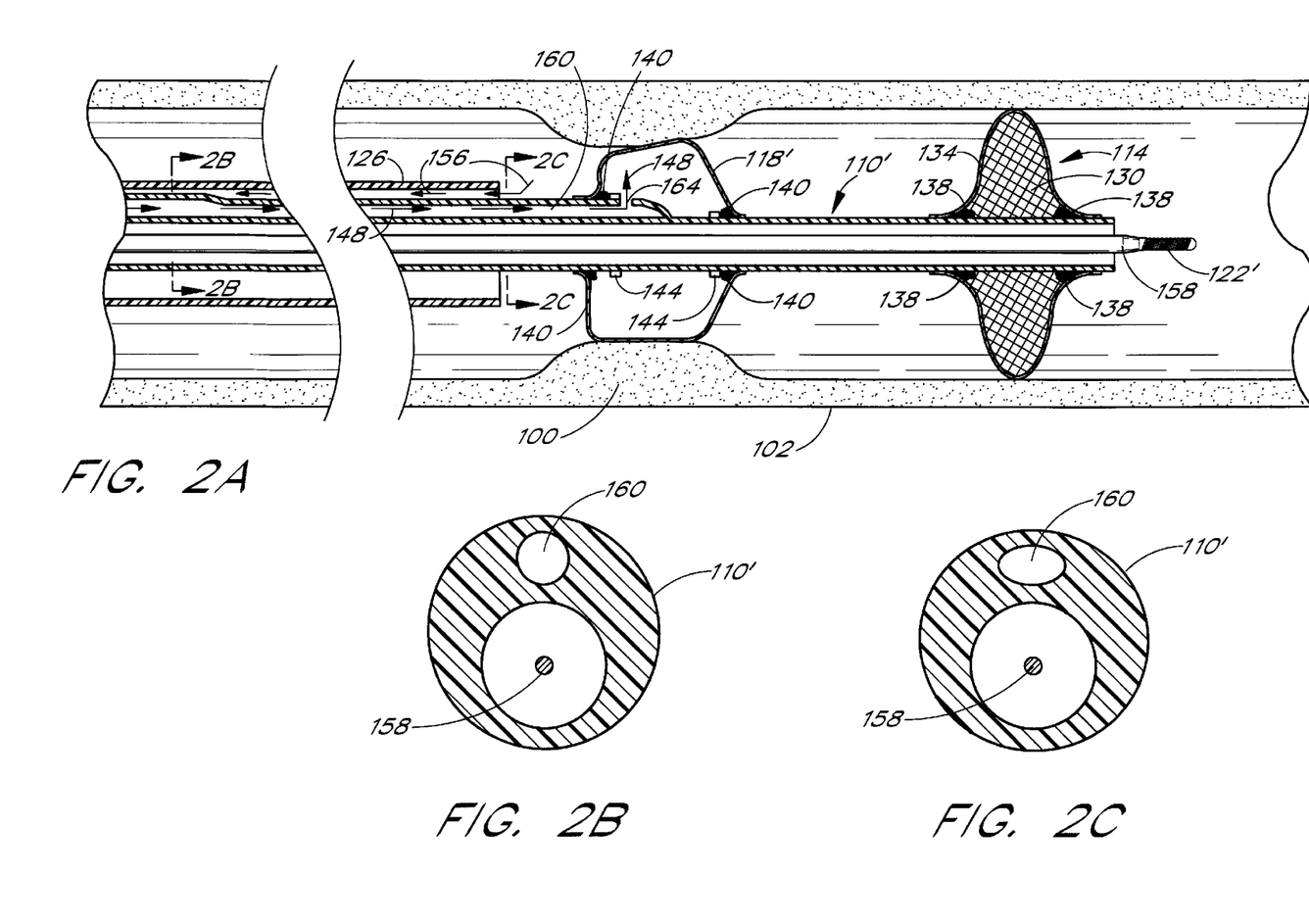
FIG. 2A is a longitudinal cross sectional view of an embodiment in which a guidewire passes through a main lumen within a catheter, and an angioplasty balloon is in fluid communication with another lumen. A catheter sheath is used to deploy a self-expanding occlusion element.
FIGS. 2B and 2C show radial cross sectional views of the embodiment of FIG. 2A, illustrating how the cross sectional profile of the inflation lumen varies along the length of the catheter.

Another embodiment is illustrated in FIG. 2A, which is substantially similar to its counterpart of FIGS. 1A and 1B. In this and the other figures, like parts are indicated with like numerals, and a primed numeral generally differs only slightly from its unprimed counterpart. In the embodiment of FIG. 2A, a guidewire 158 extends through a therapy catheter 110'. Further, a microlumen 160 forms part of the therapy catheter 110' and extends along its length. The microlumen 160 is in fluid communication with a balloon 118' (transporting fluid 148 for inflation and deflation of the balloon), and preferably adjoins the balloon through an inflation port 164. As an alternative to using the microlumen 160, a separate inflation tube may be joined to the therapy catheter 110', as discussed below in connection with FIGS. 3A and 3B. Also, the radiopaque rings in these embodiments may alternatively be located inside the therapy catheters.

The relationship between the microlumen 160 and the therapy catheter 110' is illustrated in greater detail in the radial cross sectional views of FIGS. 2B and 2C. To reduce the profile of the therapy catheter 110', the microlumen 160 is preferably as small as possible in accordance with its function, i.e., the microlumen 160 is preferably no larger than required to rapidly deflate and inflate the balloon 118'. For compliant expansion balloons, microlumen diameters (FIG. 2B) of about 0.008 inches may be satisfactory. Furthermore, in the embodiment illustrated in FIGS. 2A, 2B and 2C, the outer diameter of that part of the therapy catheter 110' residing within the patient is preferably reduced by providing the microlumen 160 with an oval cross-sectional configuration, as seen in FIG. 2C. However, the microlumen 160 may have other cross-sectional configurations that reduce the profile of the device, e.g., the microlumen may have a triangular, rectangular, or other non-oval cross sectional profile. A variety of manufacturing methods may be used in forming the microlumen 160, such as those described in Applicant's co-pending U.S. application Ser. No. 08/858,900, filed on May 19, 1997 (Atty. Docket No. PERCUS.009CP1) entitled CATHETER FOR EMBOLI CONTAINMENT, the entirety of which is hereby incorporated herein by reference.

Figure 3A:
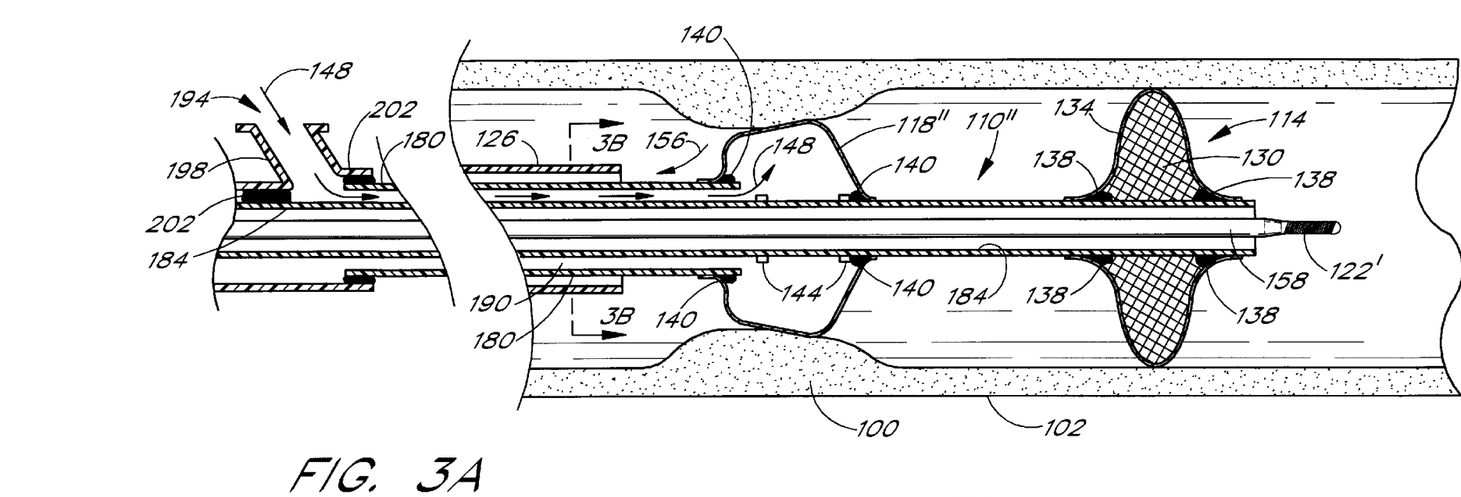
FIG. 3A is a cross sectional view of an embodiment in which the catheter includes outer and inner tubes, with the region between the outer and inner tubes acting as a conduit for inflation fluid for an angioplasty balloon. A catheter sheath is used to deploy a self-expanding occlusion element.
Figure 3B:
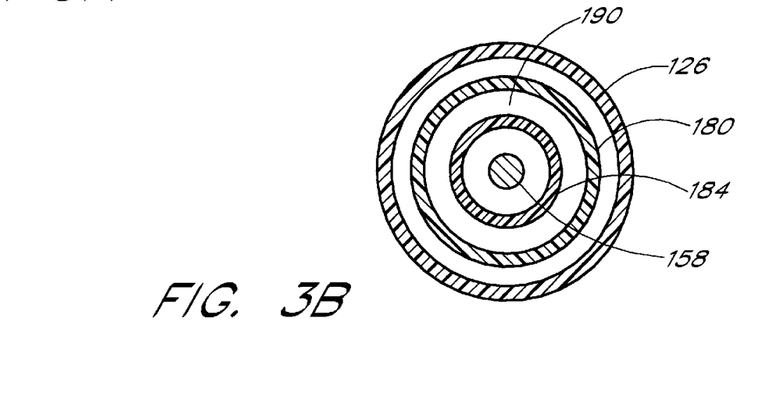
FIG. 3B is a radial cross sectional view of the embodiment of FIG. 3A.

Another embodiment that includes a self-expanding element is illustrated in FIGS. 3A and 3B. A therapy catheter 110" includes an outer tube 180 for transporting inflation fluid 148, rather than the microlumen 160 of FIGS. 2A, 2B, and 2C. The outer tube 180 is separated from an inner tube 184 of the catheter 110" by an annular region 190 through which the inflation fluid 148 flows. The annular region 190 is in fluid communication with an angioplasty balloon 118", so that the balloon can be inflated and deflated. The fluid 148 preferably enters the patient through an access port 194 (not shown in the figures of the previously discussed embodiments) of a Touhy-Borst fitting 198. Adhesive 202 can be used to secure the fitting 198 to both the outer tube 180 and the inner tube 184.

As in the embodiments shown in FIGS. 1A, 1B, 2A, 2B, and 2C, the occlusion element 114 of FIG. 3A is deployed with the catheter sheath 126. In the embodiment of FIGS. 3A and 3B, blood is preferably aspirated following deflation of the balloon 118" through the region between the outer tube 180 and the catheter sheath 126, in the direction indicated by arrow 156. In this and the other embodiments, the therapy catheter may include a separate lumen for aspirating emboli and other particulates, although this may increase the profile of the device.

2. Low profile catheters with nonself-expanding occlusion elements

Figure 4A:
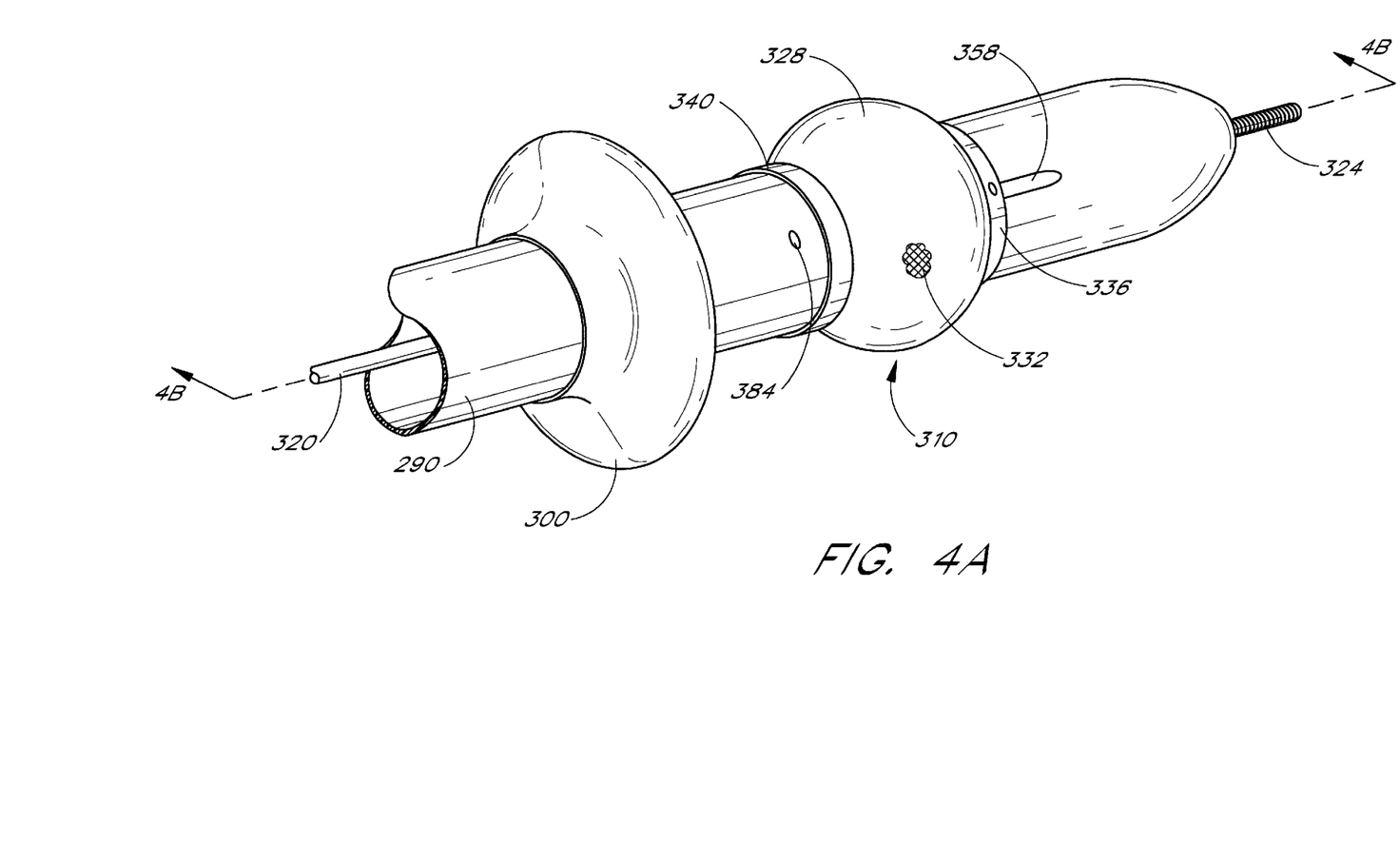
FIG. 4A is an embodiment in which an angioplasty balloon and a distal occlusion element both adjoin a therapy catheter, and the occlusion element is deployed with a pull wire.

FIG. 4A illustrates a device comprising a therapy catheter 290 to which. an angioplasty balloon 300 and an occlusion element 310 are attached, in which the occlusion element is deployed by retracting a pull wire 320. The distal end of the catheter 290 preferably includes a guidewire tip 324 to aid in the placement of the device within the patient. The occlusion element preferably includes a membrane 328 that surrounds an expansion member 332 (shown in FIG. 4A in cutaway). The expansion member 332 is similar to its self-expanding counterpart 130, except that it is not deployed with a sheath but rather with the pull wire 320, which indirectly engages a first ring member 336 attached to the expansion member 332. On the proximal end of the expansion member 332 is a second ring member 340 which is firmly secured to the catheter 290. The second ring member 340 prevents the expansion member 332 from advancing proximally beyond the second ring member, thereby forcing the expansion member 332 to expand radially so that it contacts the walls of the patient's vessel. The membrane 328 is constructed and functions similarly to its counterparts in the self-expanding embodiments to make an occlusive seal with the patient's vessel, preventing emboli from travelling downstream.

Figures 4B, 4C:
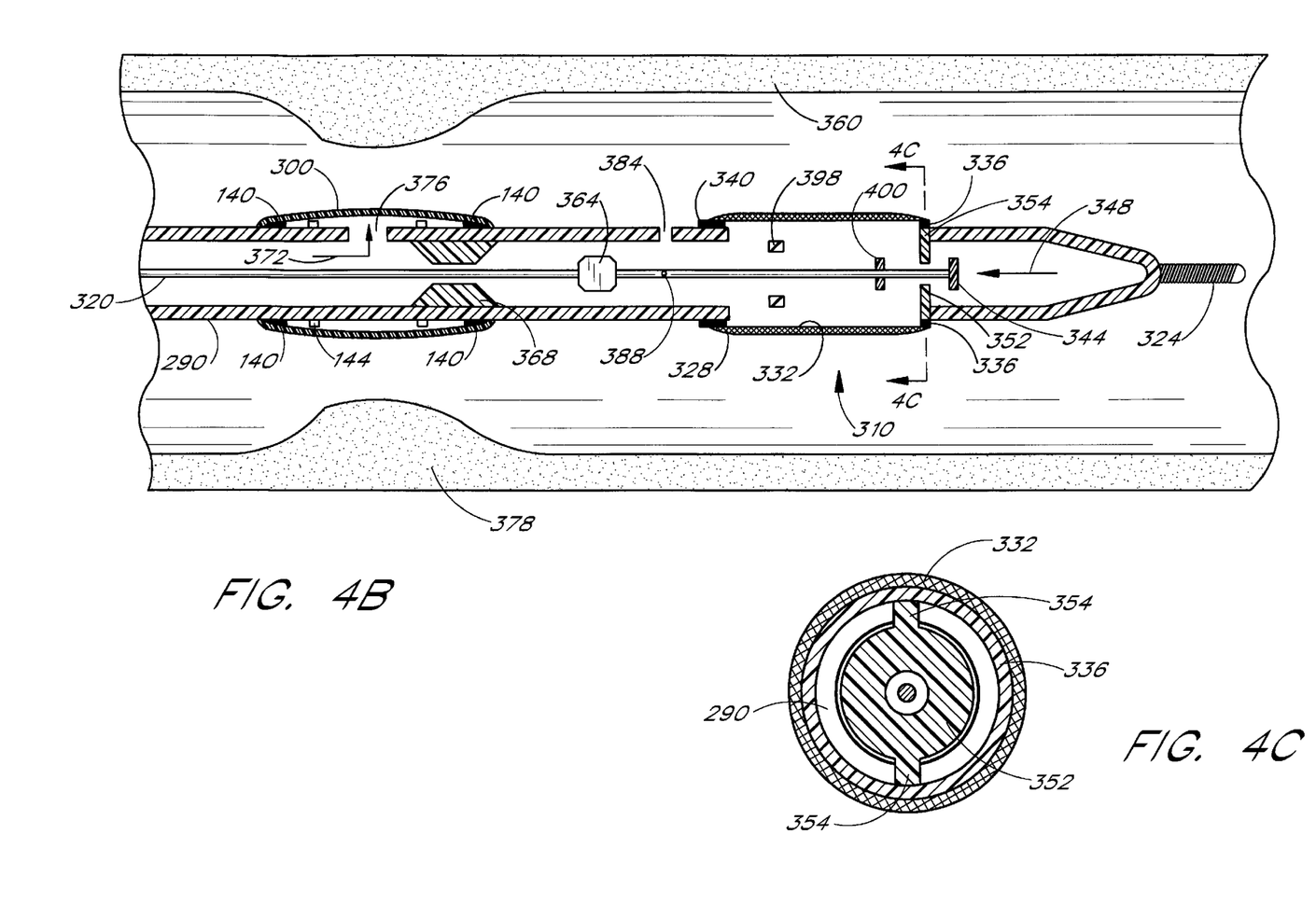
FIGS. 4B and 4D are longitudinal cross sectional views of the embodiment of FIG. 4A (undeployed and deployed, respectively), showing how a sealing member within a catheter contacts a seat to block inflation fluid from entering the distal end of the catheter. The inflation fluid passes though the catheter to inflate an angioplasty balloon.
FIG. 4C is a radial cross sectional view of a disk member which is also shown in FIGS. 4B and 4C, in which the disk member has a notch at either end. The disk member adjoins the pull wire and deploys the distal occlusion element when the pull wire is retracted.
Figure 4D:
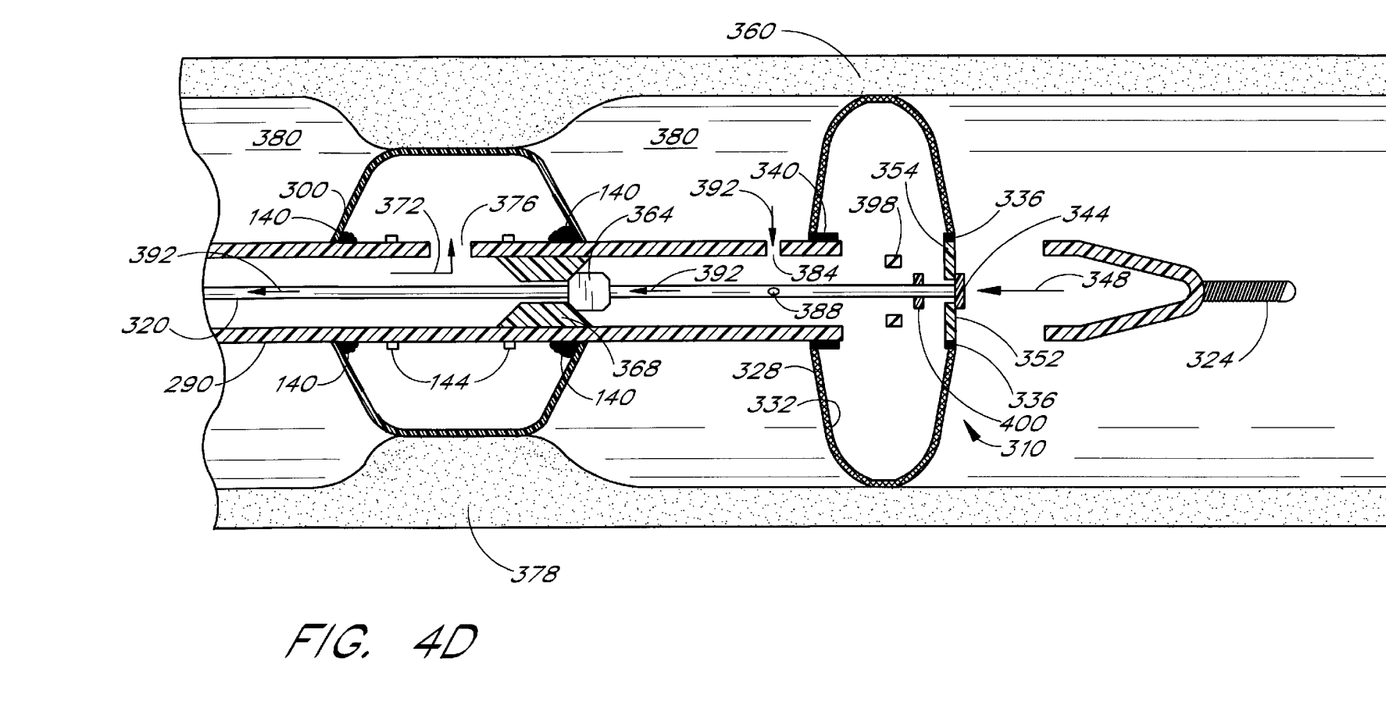

The internal workings of the device are more clearly evident in the longitudinal cross sectional view of FIG. 4B. Specifically, the pull wire 320 (which in this embodiment is preferably hollow) is attached at its distal end to a plug 344 that moves in the direction indicated by arrow 348 when the pull wire is retracted. The plug 344 engages a sliding disk member 352 that moves within the catheter 290 but preferably has 0.001–0.002" clearance with the catheter 290. The disk member 352 preferably has oppositely facing notches 354 that adjoin the first ring member 336, as illustrated in FIG. 4C. The notches 354 slide within an opening 358 (see FIG. 4A) within the catheter 290. As the first ring member 336 is moved proximally, the expansion member 332 expands radially to occlude the vessel 360, as illustrated in FIG. 4D.

When the pull wire 320 is retracted, a sealing member 364 which adjoins the pull wire mates with a seat 368 to block off the distal end of the catheter 290. This permits the balloon 300 to be inflated (FIG. 4D) by forcing fluid 372 through the catheter 290 and into the balloon, preferably through an inflation port 376. To prevent the plug 344 and the first ring member 336 from being retracted too far, which would either damage the expansion member 332 or let it expand too much and potentially damage the patient's vessel 360, a safety ring 398 is preferably used. As illustrated in FIG. 4D, safety ring 398 is firmly secured to the inner surface of the catheter 290 and blocks the first ring member 336 from advancing proximally to it.

After treating the stenosis site 378 and deflating the balloon 300 (e.g., by aspirating the fluid 372 through the inflation port 376 and the catheter 290), the volume 380 around the balloon may be aspirated through the pull wire 320 via aspiration ports 384 and 388 in the catheter 290 and the pull wire 320, respectively. Blood along with any entrapped emboli are evacuated in the direction indicated by the arrows 392.

The volume 380 may also be aspirated by moving the pull wire 320 distally to create a space between the sealing member 364 and the seat 368, and then aspirating through the aspiration port 384, past the seat 368 and out of the catheter 290. In this case, there is preferably sufficient friction between the ring member 336 and the edges of the opening 358 to keep the occlusion element 310 deployed while volume 380 is being aspirated. The occlusion element 310 may be returned to its undeployed position by moving the pull wire 320 distally so that a ring member 400 (which is attached to the pull wire) engages the disk member 352. Also, instead of aspirating the volume 380 through the catheter 290, a separate sheath that surrounds catheter 290 may be used for aspiration, analogous to the embodiment shown in FIG. 2A.

Figure 5:
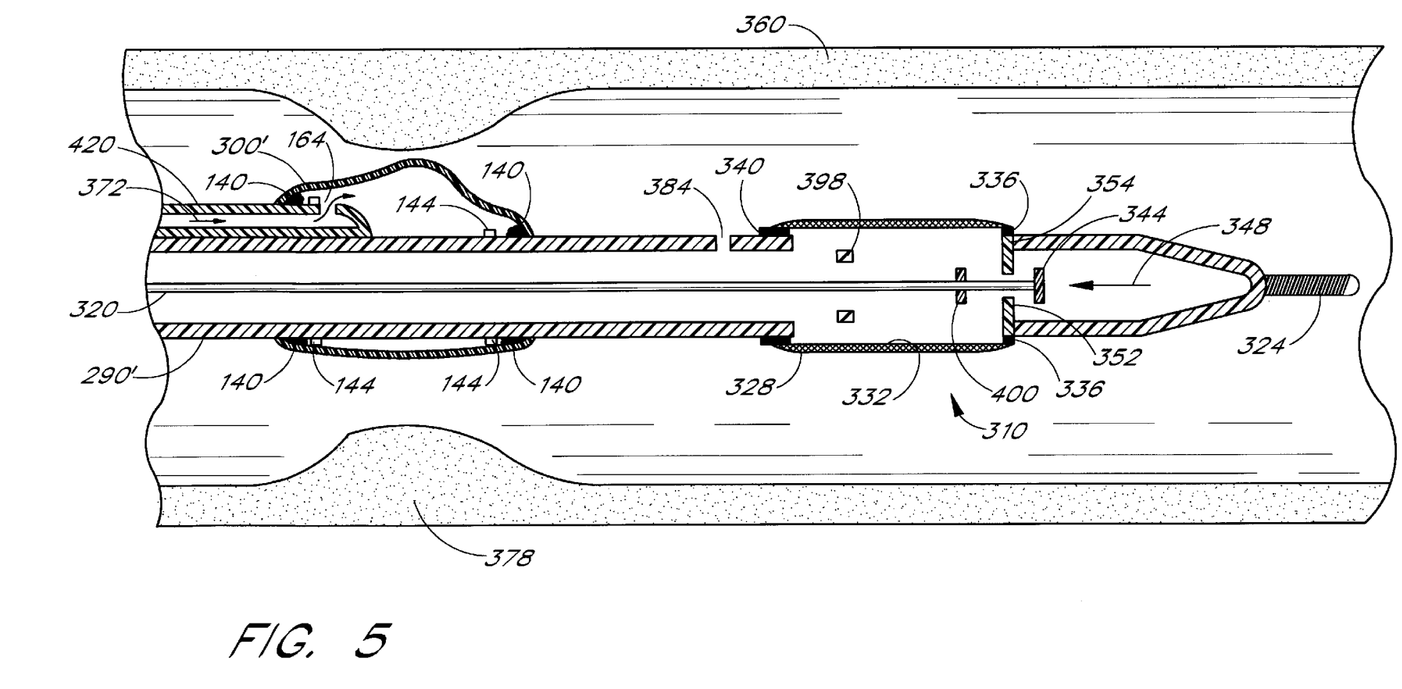
FIG. 5 is a longitudinal cross sectional view of another embodiment in which an occlusion element is deployed with a pull wire. An angioplasty balloon is inflated by passing fluid through a tube that adjoins a catheter.

Another pull wire embodiment is illustrated in FIG. 5, which is similar to the embodiment of FIGS. 4A–4D. In this embodiment, however, aspiration of the angioplasty balloon 300' is accomplished by passing fluid 372 through a separate tube 420 that is attached to the catheter 290'. The tube 420 is secured to the catheter 290' but acts functionally like the microlumen 160 of FIG. 2A. In this embodiment, there is no need for the sealing member 364 or the seat 368 of FIGS. 4B and 4C, since the angioplasty balloon 300' is not inflated through the catheter 290'. Further, aspiration of emboli can be accomplished through the catheter 290', and there is no need for an aspiration port in the pull wire 320 (such as the aspiration port 388 of FIGS. 4B and 4D).

Figure 6:
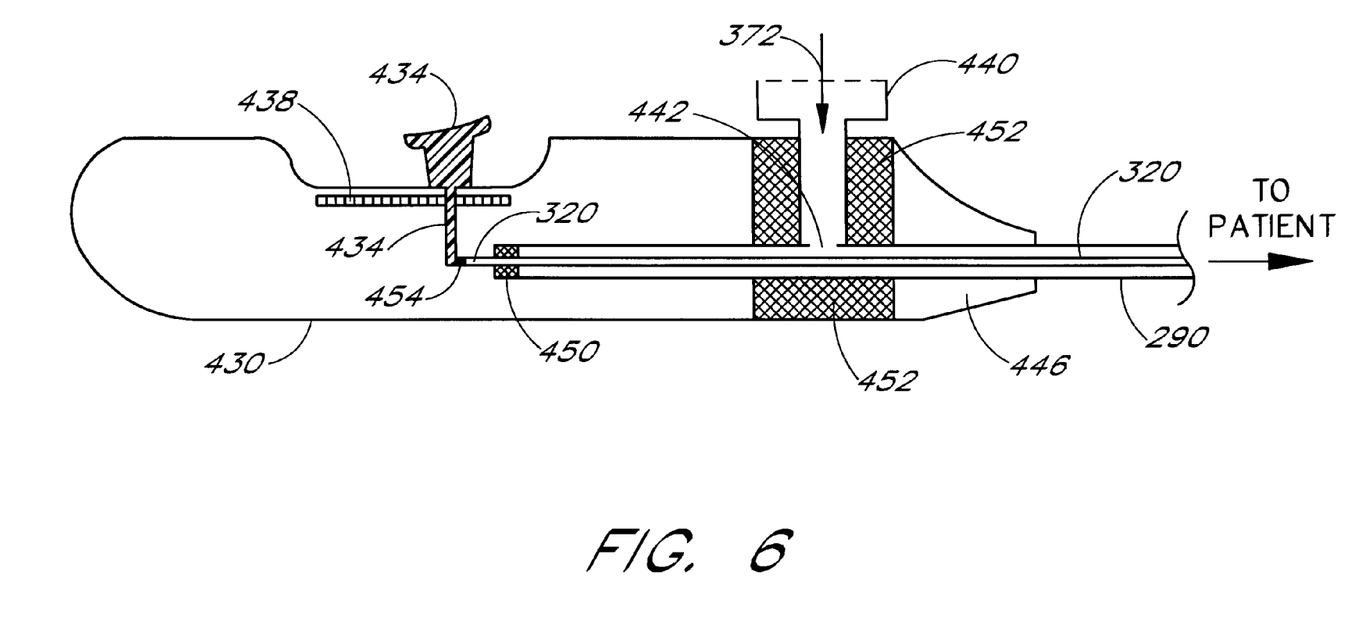
FIGS. 6 and 7 show cross sectional views of two devices for retracting the catheters of these embodiments, which use a knob and a take-up reel, respectively.
Figure 7:
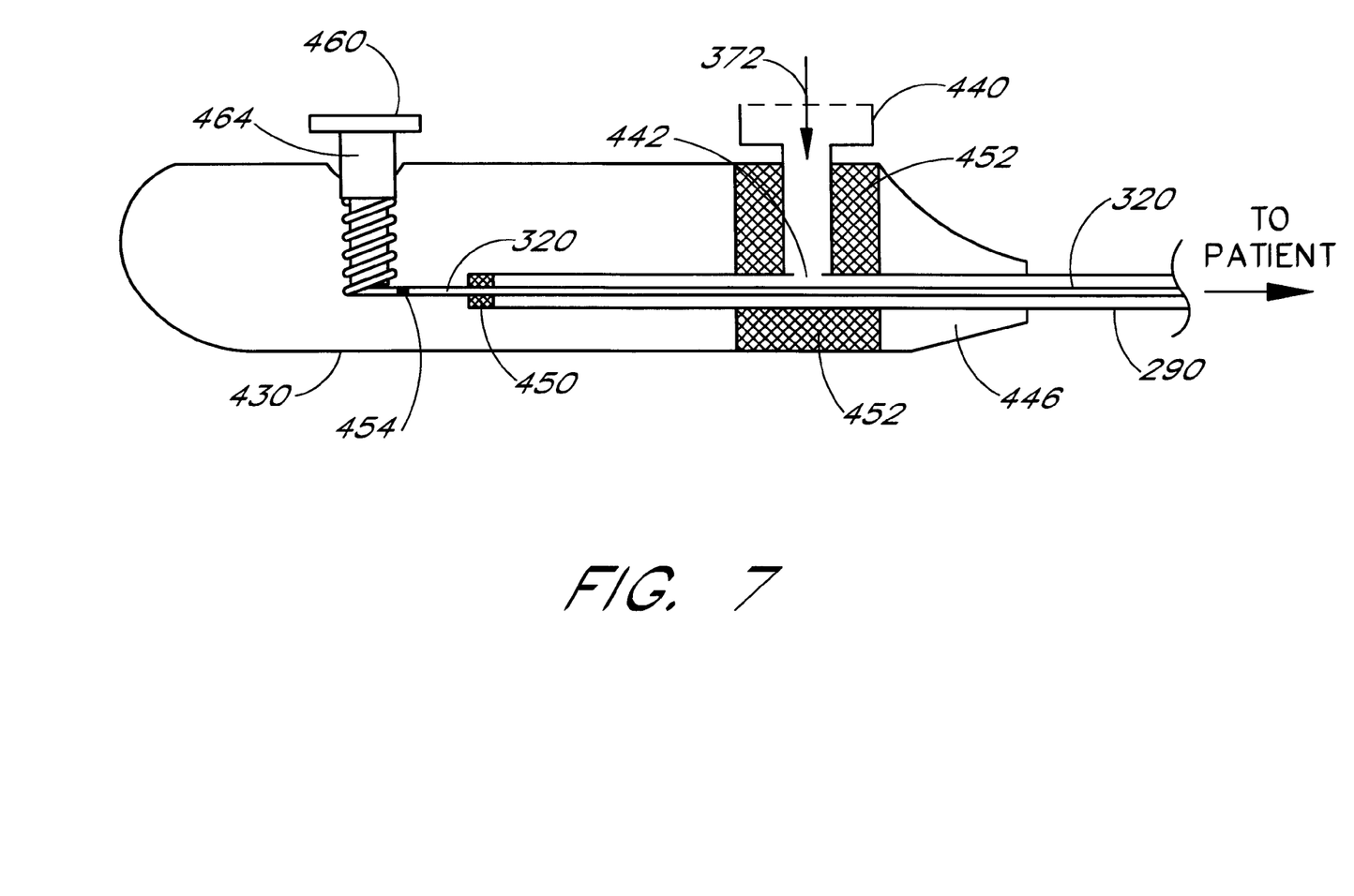

The pull wires of FIGS. 4A–D and 5 may be retracted using the techniques illustrated in FIGS. 6 and 7. In FIG. 6, the catheter 290 is secured to a handle 430 to which a knob 434 is attached. The knob 434 is secured to the pull wire 320 and slides over a series of locking ridges 438 which keep the knob from advancing or receding when the knob is not engaged. Thus, the knob 434 and locking ridges 438 function much like an electrician's razor blade retraction device. The handle 430 preferably further includes a transition region 446 for relieving strain in the handle.

If inflation fluid 372 is to be injected into the catheter 290 (as in FIGS. 4B and 4D) for inflation of an angioplasty element, then the inflation fluid may be injected through an inflation fitting 440 and then through an inflation port 442 in the catheter 290. The inflation fitting 440 is preferably secured to the handle 430 with epoxy 452.

An internal sealing element 450 as well as a sealing plug 454 within the pull wire 320 at its proximal end prevent the fluid 372 from escaping from the catheter 290. For a pull wire 320 of diameter 0.007–0.008", for example, the sealing element 450 may have a bore diameter of 0.005". In this way, the pull wire 320 is restricted or compressed as it passes through the sealing element 450, so that the fluid 372 is contained.

An alternative to the pull wire take-up apparatus of FIG. 6 is shown in FIG. 7, in which the knob 434 has been replaced by a rotating take-up reel 460 that includes a spindle 464. In this embodiment, the pull wire 320 wraps around the take-up reel 460. The diameter of the spindle 464 is preferably selected by considering the elasticity and outside diameter of the pull wire 320. For example, if the pull wire 320 has an outside diameter of 0.005" and is constructed from stainless steel (which has an elasticity of 0.4%), then the diameter of the spindle 464 is preferably at least 0.005"/0.004=1.25".

It should be understood that the scope of the present invention is not limited by the illustrations or the foregoing description thereof, but rather by the appended claims, and certain variations and modifications of this invention will suggest themselves to one of ordinary skill in the art.

What is claimed is:

1. An angioplasty apparatus, comprising:
   a catheter;
   a therapy balloon that adjoins said catheter, in which said balloon is inflatable to permit a stenosis site in a vessel to be enlarged;
   a mechanically deployed expansion element, said expansion element adjoining said catheter, in which said expansion element is expandable to prevent emboli from moving downstream;
   a pull wire that deploys said expansion element, in which said catheter surrounds said pull wire,
   a hole in said catheter so that said catheter and said balloon are in fluid communication, and
   a sealing member that adjoins said pull wire, said sealing member making an internal seal as said expansion element is deployed to isolate a distal end portion of said catheter from fluid in said balloon.

2. The apparatus of claim 1, in which said balloon is in fluid communication with the interior of said catheter, permitting said balloon to be inflated and deflated.

3. The apparatus of claim 1, in which said catheter comprises two lumens, one of said lumens being in fluid communication with said balloon.

4. The apparatus of claim 3, comprising inner and outer tubes that define said two lumens, said outer tube being in fluid communication with said balloon.

5. The apparatus of claim 1, further comprising:
   a second hole in said catheter; and
   a hole in said pull wire, wherein fluid can be aspirated from outside of said catheter to pass through said second hole in said catheter and said hole in said pull wire.

6. The apparatus of claim 5, comprising at least two lumens, one of said lumens being in fluid communication with said balloon.

7. The angioplasty apparatus of claim 1, in which expansion element is located distal to said balloon.

8. The apparatus of claim 1, wherein said expansion element is expandable to completely occlude the vessel.

9. The apparatus of claim 1, wherein said expansion element includes a membrane that contacts the vessel when said expansion element is expanded.

10. The apparatus of claim 9, wherein said membrane is perforated to allow the perfusion of blood.

11. The apparatus of claim 1, further comprising a device which retracts said pull wire.

12. The apparatus of claim 1, said sealing member contacting a seat that adjoins said catheter to make the internal seal.

13. The apparatus of claim 1, wherein said pull wire retracts a distal portion of said expansion element.

14. The apparatus of claim 13, comprising a ring member attached to a distal portion of said expansion element, said ring member sliding over said catheter as said pull wire is moved.

15. The apparatus of claim 14, further comprising a safety member attached to said catheter, said safety member preventing said ring member from advancing proximally of said safety member.

16. An angioplasty apparatus, comprising:
   a catheter,
   an angioplasty element that adjoins said catheter, in which said angioplasty element is expandable to permit a stenosis site in a vessel to be enlarged;

a mechanically deployed occlusion element, said occlusion element adjoining said catheter and located distal to said angioplasty element, in which said occlusion element is expandable to permit the vessel to be at least partially occluded;

an opening in said catheter so that said catheter and said angioplasty element are in fluid communication, and a pull wire that deploys said occlusion element and contacts an inner portion of said catheter to isolate a distal end portion of said catheter from fluid in said angioplasty element.

17. The apparatus of claim 16, in which said angioplasty element includes a balloon.

18. The apparatus of claim 16, wherein said expansion element is expandable to completely occlude the vessel.

19. An angioplasty apparatus, comprising:

a catheter;

an angioplasty element that adjoins said catheter, said angioplasty element being expandable to enlarge a stenosis site in a vessel.

a mechanically deployed expansion element, one end portion of said expansion element adjoining said catheter and another end portion of said expansion element adjoining a member that slides with respect to said catheter, wherein said expansion element is slidable over said catheter, said expansion element preventing emboli from moving downstream when expanded; and a pull wire that expands said expansion element by moving said slidable member.

20. An angioplasty apparatus, comprising:

a catheter;

an angioplasty element that adjoins said catheter, said angioplasty element being expandable to enlarge a stenosis site in a vessel, said angioplasty element comprising a balloon, said catheter including a hole such that said catheter and said balloon are in fluid communication;

a mechanically deployed expansion element, one end portion of said expansion element adjoining said catheter and another end portion of said expansion element adjoining a member that slides with respect to said catheter, said expansion element preventing emboli from moving downstream when expanded;

a pull wire that expands said expansion element by moving said slidable member, and a sealing member that adjoins said pull wire, said sealing member making an internal seal as said expansion element is deployed to isolate a distal end portion of said catheter from fluid in said balloon.

21. An angioplasty apparatus, comprising:

a catheter, an angioplasty element that adjoins said catheter, in which said angioplasty element is expandable to permit a stenosis site in a vessel to be enlarged;

a mechanically deployed expansion element that adjoins said catheter, said expansion element preventing emboli from moving downstream when expanded;

a pull wire that expands said expansion element;

an aspiration opening in said catheter, said opening permitting aspiration of a volume between said angioplasty element and said expansion element, said angioplasty element comprising a balloon, said catheter including a second hole, wherein said balloon receives inflation fluid through said second hole; and a sealing member that adjoins said pull wire, said sealing member making an internal seal as said expansion element is deployed to isolate a distal end portion of said catheter from fluid in said balloon.

22. An angioplasty apparatus. comprising:

a catheter, an angioplasty element that adjoins said catheter, in which said angioplasty element is expandable to permit a stenosis site in a vessel to be enlarged;

a mechanically deployed expansion element that adjoins said catheter, said expansion element preventing emboli from moving downstream when expanded:

a pull wire that expands said expansion element: and an aspiration opening in said catheter, said opening permitting aspiration of a volume between said angioplasty element and said expansion element, said pull wire including a hole which is in fluid communication with said aspiration opening, thereby permitting fluid from said volume to be aspirated through a lumen in said pull wire.

23. An angioplasty apparatus, comprising:

a catheter:

an angioplasty element, said angioplasty element adjoining said catheter and treating a stenosis site in a vessel;

an emboli protection element, said emboli protection element adjoining said catheter and preventing the migration of emboli; and a pull wire that activates said emboli protection element while enabling actuation of said angioplasty element, wherein said emboli protection element is slidable over said catheter.

24. An angioplasty apparatus, comprising:

a catheter:

an angioplasty element, said angioplasty element adjoining said catheter and treating a stenosis site in a vessel;

an emboli protection element, said emboli protection element adjoining said catheter and preventing the migration of emboli:

a pull wire that activates said emboli protection element while enabling actuation of said angioplasty element; and a sealing member that adjoins said pull wire, said sealing member making an internal seal as said emboli protection element is deployed to isolate a distal end portion of said catheter from fluid in said angioplasty element.

* * * * *